(12) United States Patent
Rotolo

(10) Patent No.: US 8,011,371 B2
(45) Date of Patent: Sep. 6, 2011

(54) SURGICAL DRAPE WITH PATIENT-ORIENTED WINDOW AND METHOD OF PRODUCTION

(75) Inventor: Peter J. Rotolo, Winchester, MA (US)

(73) Assignee: Peter J. Rotolo, Winchester, MA (US)

( * ) Notice: Subject to any disclaimer, the term of this patent is extended or adjusted under 35 U.S.C. 154(b) by 323 days.

(21) Appl. No.: 12/363,519

(22) Filed: Jan. 30, 2009

(65) Prior Publication Data
US 2010/0192960 A1 Aug. 5, 2010

(51) Int. Cl.
A61B 19/08 (2006.01)
A61B 19/00 (2006.01)

(52) U.S. Cl. ........................................ 128/854; 128/849

(58) Field of Classification Search .................. 128/846, 128/849, 853, 854–856
See application file for complete search history.

(56) References Cited

U.S. PATENT DOCUMENTS

| | | | |
|---|---|---|---|
| 4,384,573 A | 5/1983 | Elliott | |
| 4,489,720 A | 12/1984 | Morris et al. | |
| 4,574,796 A | 3/1986 | Lundstrom et al. | |
| 4,616,642 A | 10/1986 | Martin et al. | |
| 4,905,710 A | 3/1990 | Jones | |
| 5,209,243 A | 5/1993 | Glassman | |
| 5,586,563 A | 12/1996 | Newman | |
| 5,860,420 A | 1/1999 | Wiedner et al. | |
| 5,875,780 A | 3/1999 | Rodriquez | |
| 5,960,794 A | 10/1999 | Shaw | |
| 6,966,320 B1 | 11/2005 | Baynes | |
| 7,044,132 B2 | 5/2006 | Masini | |
| 7,802,313 B2 * | 9/2010 | Czajka | ................................ 2/51 |
| 2002/0069882 A1 | 6/2002 | Sklar | |
| 2003/0196668 A1 | 10/2003 | Harrison et al. | |
| 2005/0126577 A1 | 6/2005 | Griesbach, III | |
| 2006/0207609 A1 * | 9/2006 | Gil et al. | ........................ 128/849 |
| 2007/0062544 A1 | 3/2007 | Rauk Bergstrom et al. | |

FOREIGN PATENT DOCUMENTS

| | | |
|---|---|---|
| EP | 2 326 100 | 12/1998 |
| JP | 2004-81566 | 3/2004 |

* cited by examiner

Primary Examiner — Patricia Bianco
Assistant Examiner — Tarla Patel

(57) ABSTRACT

A surgical drape includes a flexible opaque sheet configured to satisfy barrier performance requirements of AAMI PB70: 2003, and a flexible transparent sheet disposed within the opaque sheet to form a window sized and shaped to permit the patient to view the surgical procedure therethrough. The window is configured to satisfy the barrier performance requirements of AAMI PB70:2003, and a flexible, opaque cover is sized and shaped to substantially match that of the window. One or more releasable fasteners are configured to releasably dispose the cover in superposed relation with the window, to selectively cover and uncover the window.

26 Claims, 6 Drawing Sheets

SURGICAL DRAPE WITH PATIENT-ORIENTED WINDOW AND METHOD OF PRODUCTION

BACKGROUND

1. Technical Field

This invention relates to a surgical drape, and more particularly to a surgical drape for Caesarian section procedures, the drape having a coverable transparent window oriented to allow a patient and her husband or other companion to selectively view the birth of their child and other aspects of the procedure.

2. Background Information

When preparing a patient for surgery, the area of the incision (the surgical area or surgical field) is sterilized to help prevent infection. Sterilized surgical drapes are then typically placed about the sterilized surgical area. The surgical drapes provide a barrier which helps to isolate the sterilized surgical area from non-sterilized surroundings. During surgical operations such as Caesarian section procedures, the surgical drape also serves to protect the patient, and any nearby observers (e.g., the father or other family members) from fluids released during the procedure.

These conventional surgical drapes are designed and deployed to provide the surgical team with an unencumbered view of the surgical area. Little or no consideration, however, is typically given to enabling the patient or family member to view the procedure. Rather, for procedures in which the patient is conscious, conventional drapes are generally used to intentionally block the patient's view of the surgical area. For example, a Caesarian section drape customarily forms a relatively large vertical overhang, which effectively forms an opaque wall between the patient's face and the surgical field. This wall disadvantageously tends to obstruct the parents' view of the birth.

In order to allow the parents to view the birth, the drape must be lowered or removed, potentially exposing the surgical field to infection. Lowering or removing the surgical drape also potentially exposes the parents to blood and other fluid from the operation, while also permitting the parents to view other aspects of the surgery (e.g., the surgical incision, stitching, etc.), that they may not wish to see.

A need therefore exists for a sterilizable surgical drape for surgical procedures, such as Caesarian sections, which provides the desired barrier functionality, while selectively enabling the patient (and family members) to view the birth of their child as well as some aspects of the surgery, and blocking the view of other aspects of the procedure.

SUMMARY

One aspect of the invention includes a surgical drape for use in a surgical procedure on a patient. The surgical drape includes a flexible opaque sheet configured to satisfy barrier performance requirements of AAMI PB70:2003, and which is configured for gas sterilization. A flexible transparent sheet is disposed within the opaque sheet to form a window sized and shaped to permit the patient to view the surgical procedure therethrough. The window is configured to satisfy the barrier performance requirements of AAMI PB70:2003, is configured for gas sterilization, and is sealed along substantially its entire periphery so that the seal satisfies the barrier performance requirements of AAMI PB70:2003. An opaque cover sized and shaped to substantially match that of the window is provided with releasable fasteners to releasably place the cover in over the window, so that the cover may be used to selectively cover and uncover the window. At least a portion of the cover is non-removably fastened to the drape.

Another aspect of the invention includes a surgical drape for use in a surgical procedure on a patient. The surgical drape includes a flexible opaque sheet configured to satisfy barrier performance requirements of AAMI PB70:2003, and a flexible transparent sheet disposed within the opaque sheet to form a window sized and shaped to permit the patient to view the surgical procedure therethrough. The window is also configured to satisfy the barrier performance requirements of AAMI PB70:2003. A flexible, opaque cover is sized and shaped to substantially match that of the window. One or more releasable fasteners are configured to releasably dispose the cover in superposed relation with the window, to selectively cover and uncover the window.

In yet another aspect of the invention, a surgical method includes providing a surgical drape having a flexible transparent window, a flexible cover sized and shaped to match the window, and a plurality of releasable fasteners configured to releasably secure the cover in superposed relation with the window, the drape meeting the barrier performance requirements of AAMI PB70:2003. The drape is hung over a patient, to form a substantially vertical barrier between the patient's head and the patient's surgical field. The window is closed using the releasable fasteners to secure the cover over the window. Aspects of the surgical procedure are then performed in the surgical field while the patient's view of the surgical field is blocked by the closed window. The fasteners are then released to allow the patient to view the surgical field through the window, allowing the parents to enjoy seeing the birth of their child. Additional aspects of the surgical procedure may then be performed in the surgical field, within view of the patient through the window. The window is then re-closed, and further aspects of the surgical procedure are performed in the surgical field, while the patient's view of the surgical field is blocked by the closed window.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
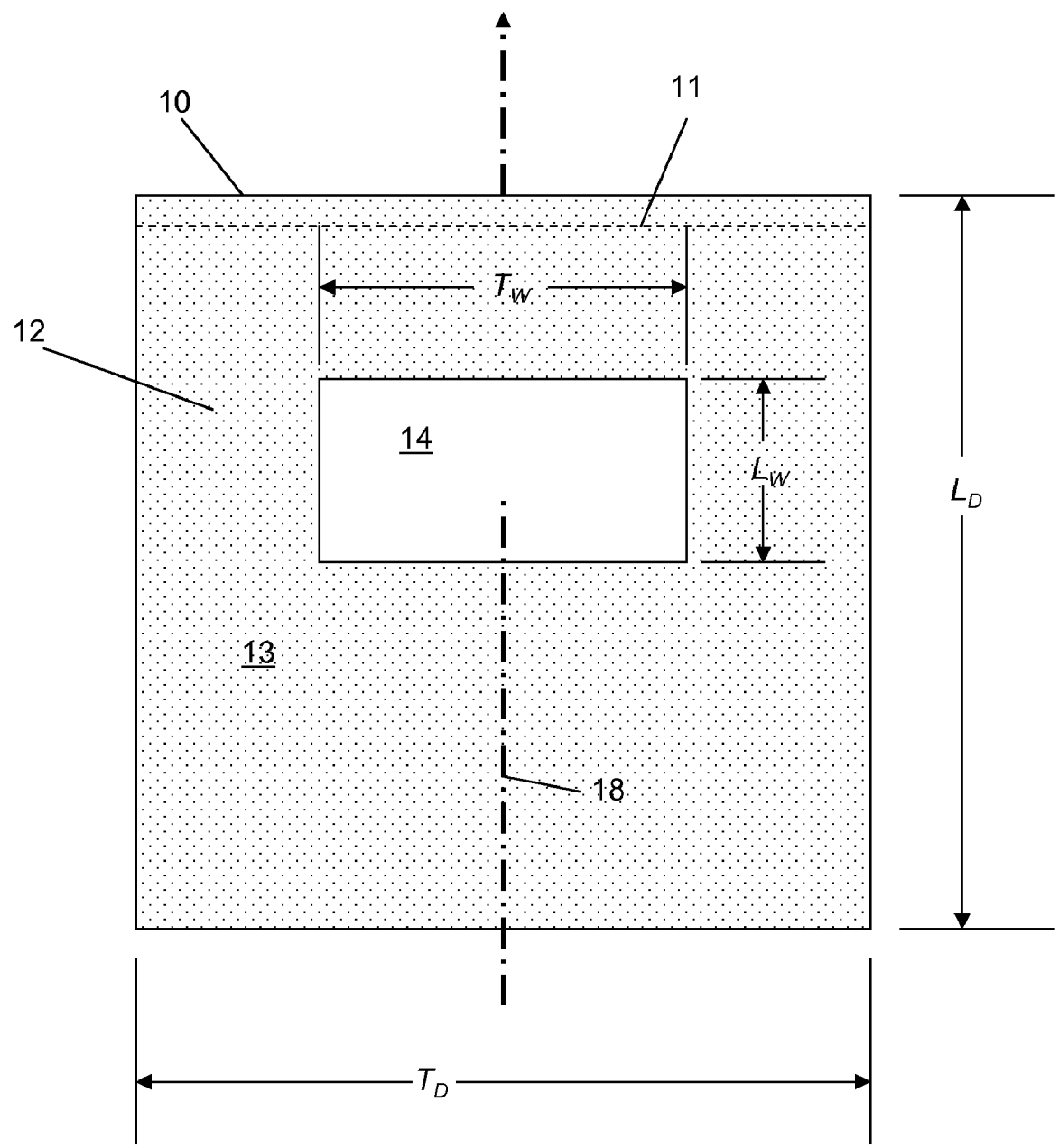
FIG. 1 is a schematic front elevational view of an embodiment of the invention.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features are indicated with similar reference numerals.

Where used in this disclosure, the term "patient side" or "front side" refers to a side of the surgical drape facing the head of the patient. "Surgical side" or "rear side" refers to a side of the surgical drape opposite the patient side, i.e., which does not face the head of the patient. In addition, it should be noted that the mother during a Caesarian section may have a loved one/family member present. For convenience, this specification refers collectively to the mother and loved one/family member as the "parents".

An aspect of the invention was the realization by the instant inventor that during Caesarian section procedures, parents often wish to view the birth of the child, but that such viewing was thwarted or rendered substantially impossible by conventional surgical drapes. As discussed above, these conventional drapes are typically deployed in a manner which blocks the parents' view. As also discussed, lowering the drape to allow the parents to see the birth has drawbacks including potentially exposing the surgical area to infection, while also exposing the parents to aspects of the surgery from which they may wish to be shielded. The inventor determined that a sterilizable clear plastic window disposed on the drape, would not compromise the sterility of the surgical area (or the ability to sterilize the drape for re-use), while allowing the parents to view the birth. The inventor also determined that a sterilizable, selectively deployable cover integrated into the window/drape, may be used to enable the parents to view the birth, and to shield the parents from other aspects of the procedure.

For example, during the preliminary steps of a typical Caesarian section procedure, the cover may be deployed over the window to block the parents' view. The surgical team may then remove the cover to permit the parents to view the birth, while protecting both the parents and the sterility of the surgical field. The cover may be replaced for the remainder of the procedure.

Turning now the Figures, embodiments of the present invention will be discussed in detail. Referring to FIG. 1, drape 10, as seen from patient side 12 thereof, includes an opaque sheet material 13 having a window 14. As discussed above, window 14 is sized and shaped to provide the patient undergoing the procedure with a relatively unobstructed view of the surgical field when the drape is suspended over the patient in a conventional manner. In this regard, drape 10 is provided with a support engagement, such as hemmed portion 11 through which a drape support may extend, as discussed in greater detail hereinbelow with respect to FIG. 2. A patient may thus observe a surgical procedure through window 14 along patient viewing axis 18, when the cover 22 (FIGS. 2-4) is opened.

The opaque sheet material 13 may be substantially any material commonly used for surgical drapes, i.e., substantially any sheet material capable of meeting the barrier performance requirements of AAMI PB70:2003 *Liquid Barrier Performance and Classification of Protective Apparel and Drapes Intended for Use in Health Care Facilities*, as established by the Association for the Advancement of Medical Instrumentation (Arlington, Va.). Moreover, although it is contemplated that the embodiments of drape 10 shown and described herein may be disposable, in particular embodiments, drape 10 is sterilizable (e.g., gas sterilizable), to facilitate re-use.

Examples of sheet material that may be suitable for various embodiments of drape 10 include woven or non-woven absorbent laminates, barrier composites, and barrier fabrics, such as those available from Precision Fabrics Group, Inc. (Vinton, Va.). SMS non-woven material (spunbond-meltblown-spunbond) material, and/or 3M™ Ioban™ 2 antimicrobial drape material available from 3M (St. Paul, Minn.) may also be used in some applications.

Window 14 may be fabricated from any one or more materials, which are substantially transparent and flexible. In particular embodiments, the window material is capable of meeting the barrier performance requirements of the aforementioned AAMI PB70:2003 standard. Examples of potentially suitable materials include polymeric (plastic) sheet materials, e.g., polyethylene (PE), polyvinylchloride (PVC), polypropylene (PP), and combinations or mixtures thereof.

As mentioned above, in particular embodiments, the window is fabricated from a material that is capable of being sterilized by gas-sterilization techniques commonly used in hospitals and other medical facilities. Examples of gas-sterilization techniques usable with the various embodiments discussed herein, include those using Ethylene Oxide (EtO) gas, e.g., those known as gas diffusion sterilization techniques.

Window 14 is secured to the opaque sheet material 13 with a seal that meets or exceeds the barrier performance of the drape material. For example, a suitable seal may be provided by heat fusion, ultrasonic welding, chemical adhesives, and/or combinations thereof, depending on the particular materials used for sheet 13 and window 14. Moreover, although window 14 is shown and described as being bounded along its entire periphery by sheet material 13, it should be recognized that in some embodiments, window 14 may be disposed along an edge of the drape, so that a portion of the periphery of window 14 forms an outer edge of drape 10, and thus is not secured to material 13.

To help insure an unobstructed patient view in a wide range of applications, it has been found that window 14 may be relatively large, e.g., having a longitudinal dimension ($L_W$) of about 10-20 inches (25-51 cm), and a transverse dimension ($T_W$) of about 20-30 inches (51-76 cm). These dimensions provide a viewing area within a range of about 200 to 600 in$^2$ (1250-3900 cm$^2$). In particular embodiments, which may be useful in a majority of Caesarian section procedures, the window 14 may have a longitudinal dimension $L_W$ of about 15 inches (38 cm), and a transverse dimension $T_W$ of about 24 inches (61 cm), to provide a viewing area of approximately 360 in$^2$ (2300 cm$^2$). While the drape 10 may be of substantially any desired size and shape, typical overall dimensions of drape 10 may include a longitudinal dimension $L_D$ of about 110 inches (279 cm) to about 130 inches (330 cm), and a transverse dimension $T_D$ of about 90 inches (229 cm) to about 110 inches (279 cm). In a particular embodiment, $L_D$ is about 120 inches (305 cm) and $T_D$ is about 100 inches (254 cm).

Moreover, while in the embodiments shown, window 14 is generally rectangular, the skilled artisan should recognize that the window may be of substantially any convenient size and shape, including circular, oval, trapezoidal, and/or other polygonal or ovoid shapes, etc., suitable for enabling a patient to view the surgical field. Still further, the desired window area may be provided by a single window, or by a series of smaller windows disposed in spaced relation to one another to form a divided-light window effect, without departing from the scope of the present invention.

These embodiments thus represent an improvement over currently available surgical drapes, which as mentioned above, are configured primarily to help maintain a sterile surgical field at the area of the incision, and to protect the patient/family members from fluids, but which are not configured to allow the patient to selectively view aspects of the surgical procedure.

Figure 2:
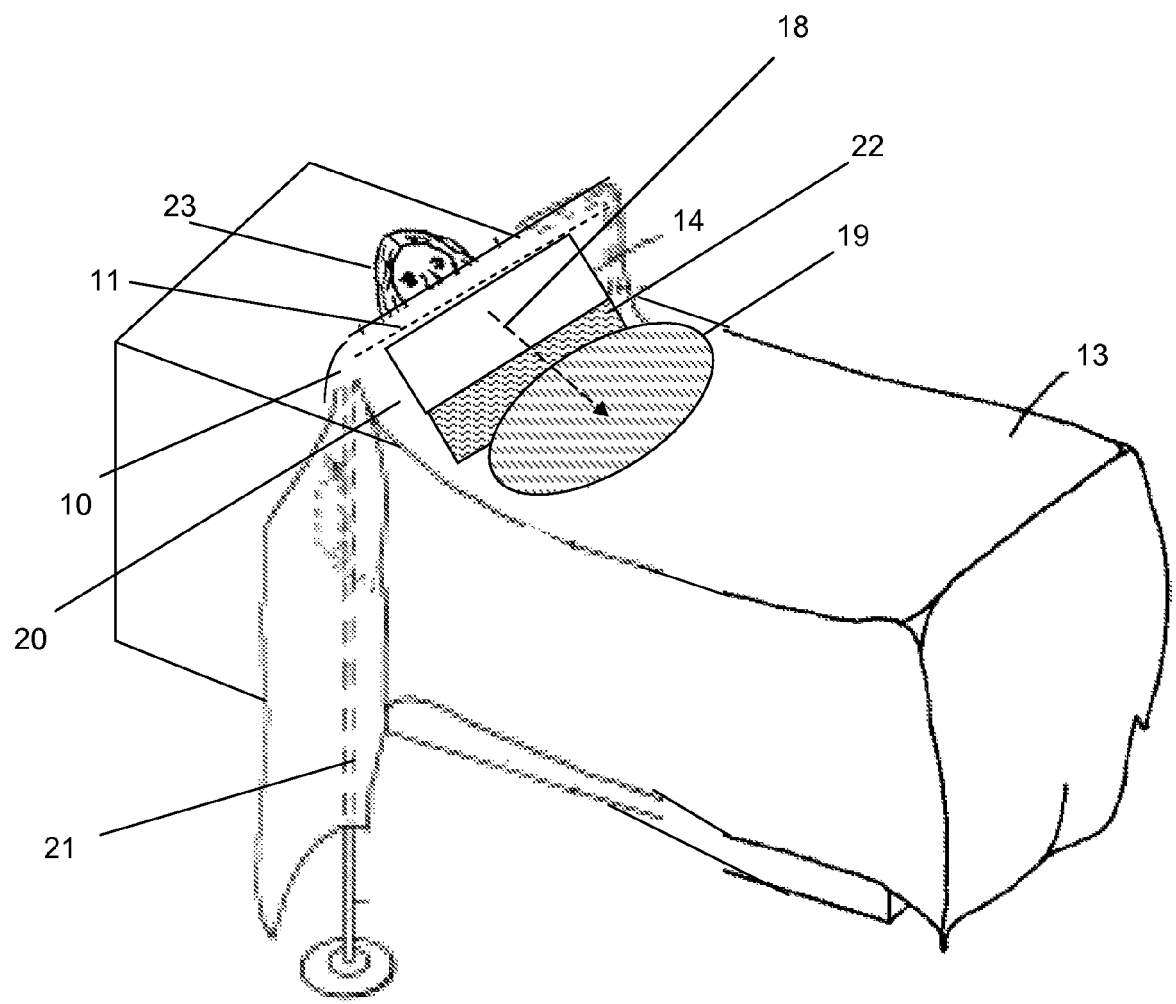
FIG. 2 is a perspective view of the embodiment of FIG. 1 in a representative application.

Turning to FIG. 2, a drape 10 is disposed in a representative application. As shown, the drape is supported in a conventional manner, e.g., by a generally U-shaped pole 21 that extends vertically from the floor next to a patent's bed 13, and then horizontally over the patient as shown. The horizontal portion of pole 21 supports the upper margin of drape 10, such as by passing through a support engagement, such as a hemmed portion 11, to suspend the drape over the patient 23.

Alternatively, the drape may be suspended between conventional I.V. (intravenous) poles extending vertically on either side of the patient (i.e., without a horizontal tubing portion). The drape may thus be clipped to the i.v. poles and suspended therebetween to suspend the drape over the patient substantially as shown.

When so disposed, the patient 23 may look through window 14, along patient viewing axis (sight line) 18, to observe the surgical area 19. In this example, cover 22 is disposed on the surgical side 20 of the drape, to allow the surgical team to determine when to open and close the cover. In alternate embodiments and/or applications, however, the cover may be disposed on the patient side of the drape, such as to enable family members or the patient to operate the cover.

Figure 3:
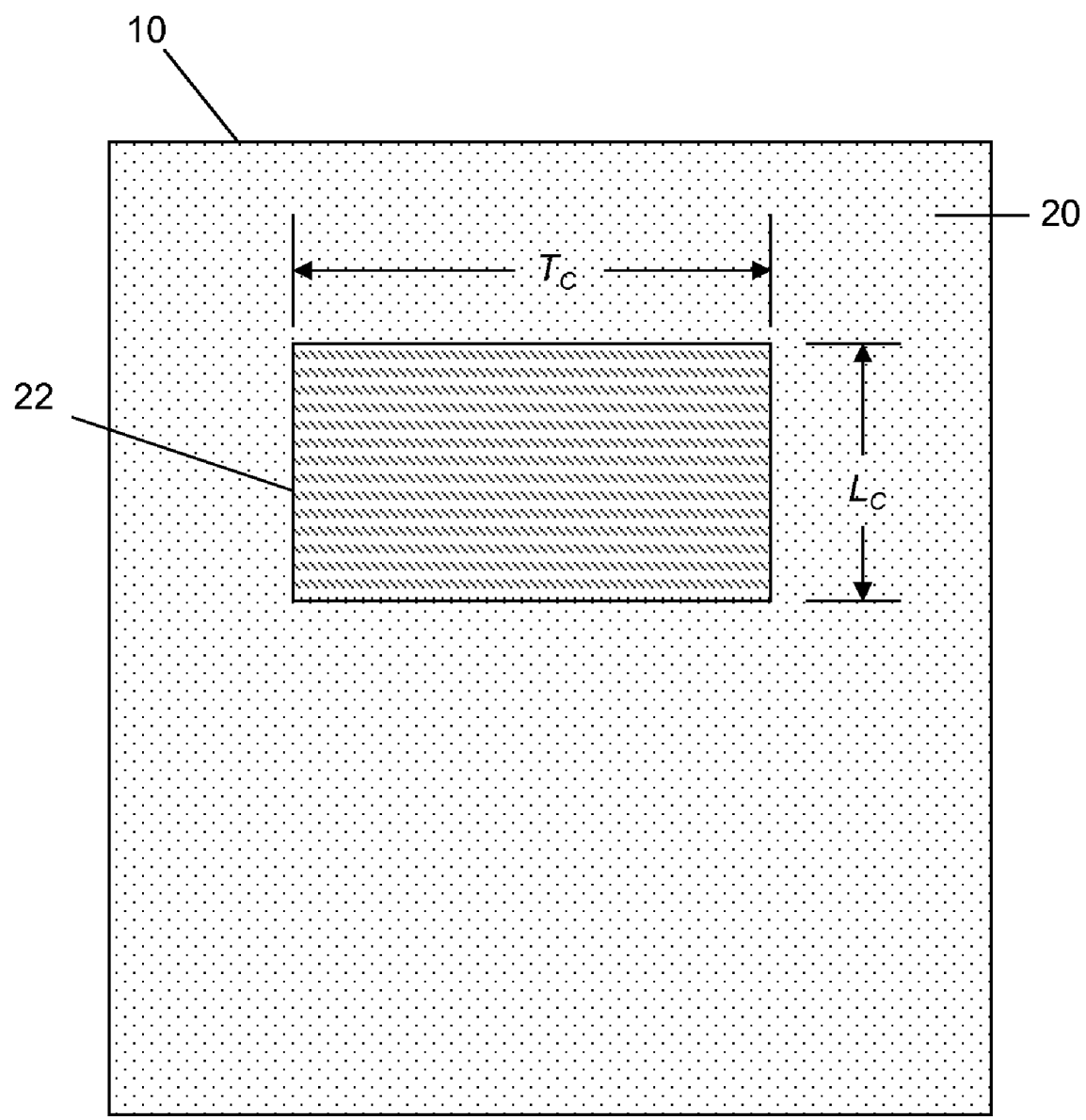
FIG. 3 is a schematic rear elevational view of the embodiment of FIG. 1, with a cover in a closed configuration.
Figure 4:
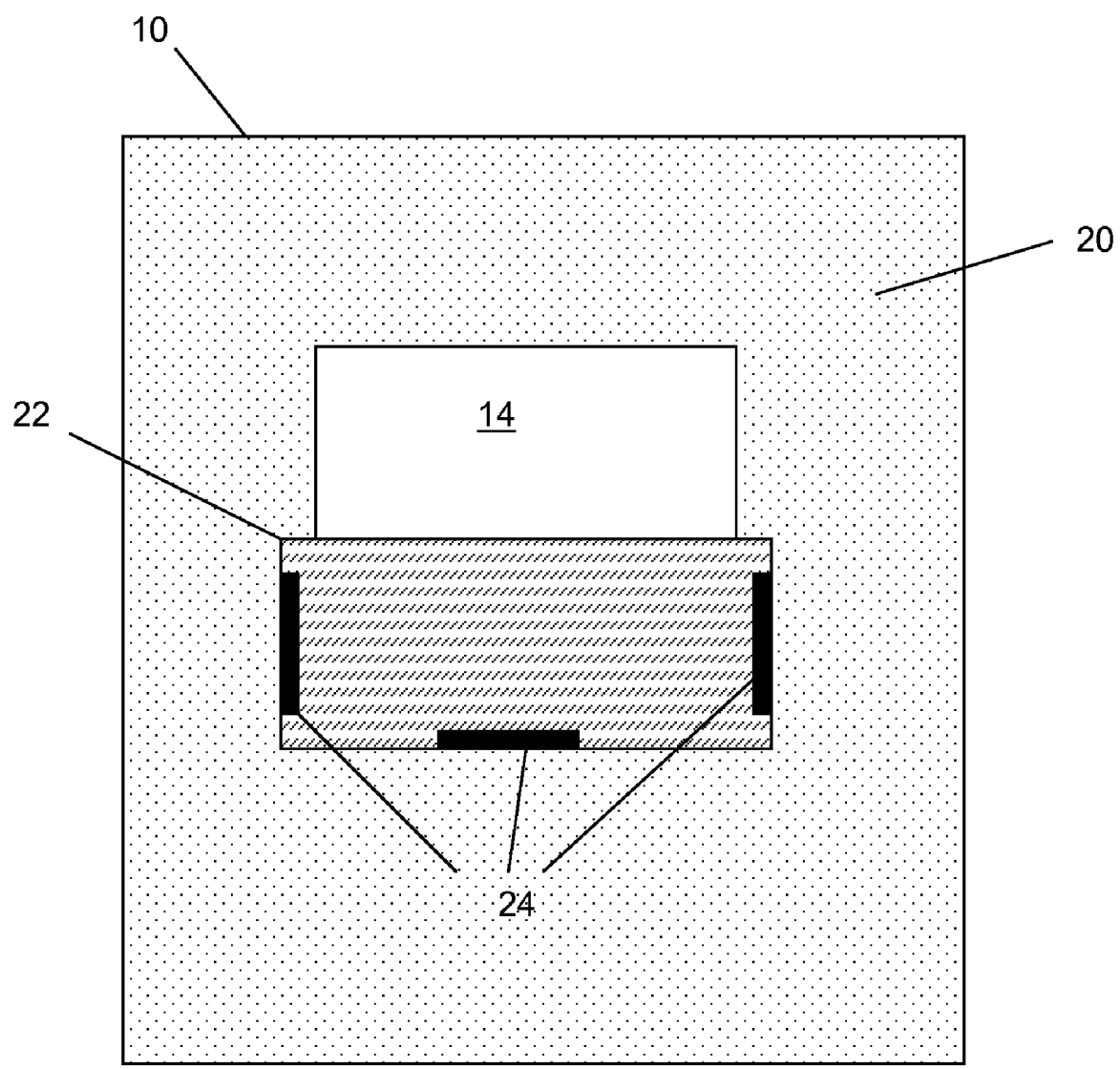
FIG. 4 is a schematic rear elevational view of the embodiment of FIG. 1, with the cover in an open configuration.

Turning to FIG. 3, the surgical side 20 of drape 10 is shown, with cover 22 in its closed position, i.e., secured in position by releasable fasteners 24 (FIG. 4). As also shown, cover 22 is sized and shaped to match the window. Therefore, the transverse dimension $T_C$ and longitudinal dimension $L_C$ of cover 22 may be approximately equal to or slightly larger than the corresponding dimensions $T_W$ and $L_W$ of window 14, shown in FIG. 1.

Referring now to FIG. 4, cover 22 is shown in its open position (on surgical side 22), which permits the patient to view the procedure. In this orientation, releasable fasteners 24 may be seen, which are disposed in spaced relation along the periphery of cover 22. Substantially any type of releasable fasteners may be used, including mechanical and chemical fasteners such as mechanical snaps, ties, and/or adhesives such as releasable adhesives similar to that used in Post-It® notes (3M, Minneapolis, Minn.), etc. In particular embodiments, the releasable fasteners 24 include conventional hook and loop fasteners, e.g., VELCRO® fasteners (Velcro Industries B.V.). The cover may be re-closed by re-fastening the releasable fasteners 24 to the drape 10 along the periphery of window 14.

In various embodiments, cover 22 may be completely removable from the drape. Alternatively, it may be permanently affixed to the drape, e.g., along a lower edge of the window in the orientation shown, to prevent the cover from becoming lost or misplaced when opened, or during sterilization, etc.

Figure 5:
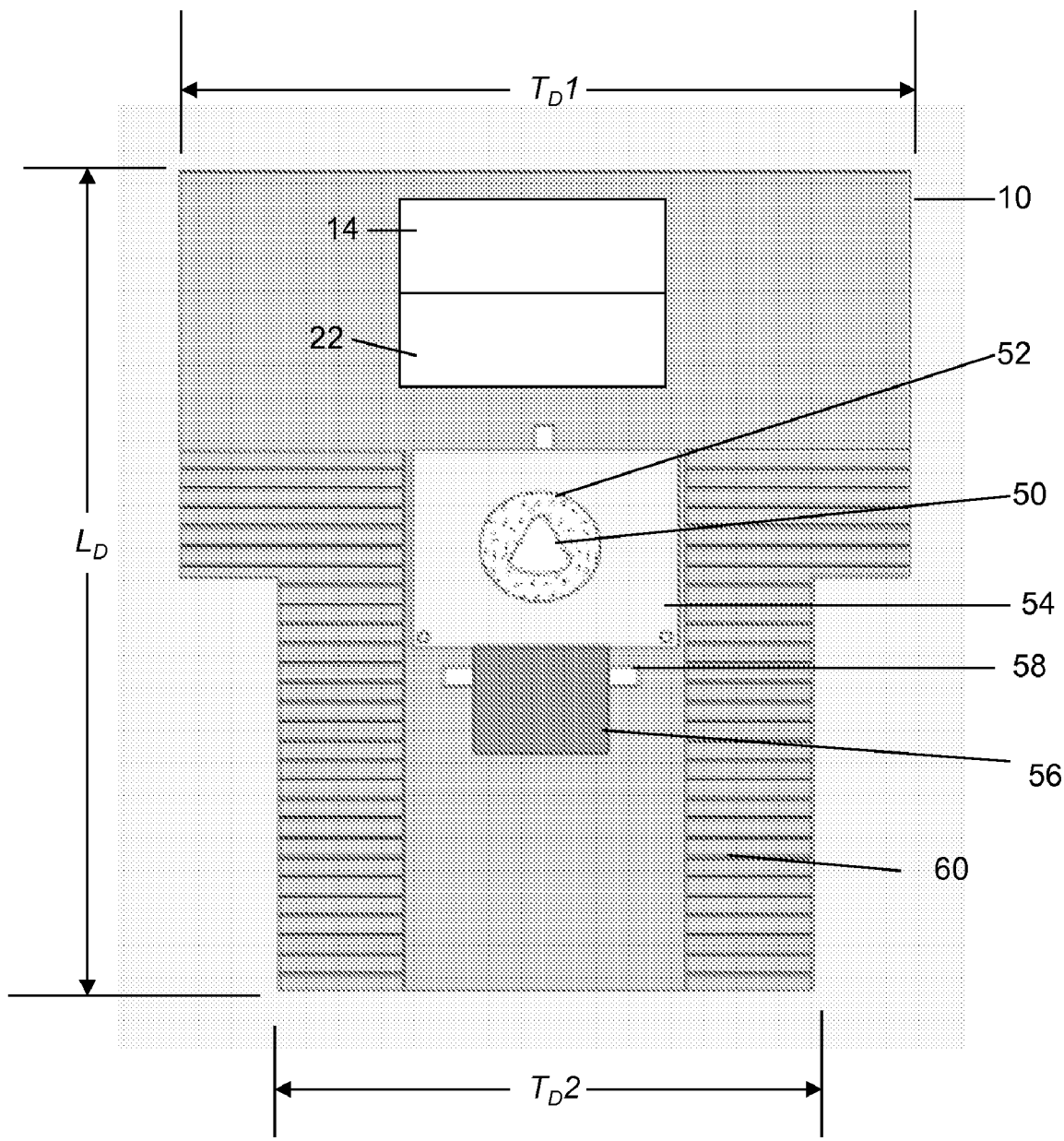
FIG. 5 is a schematic front elevational view of an alternate embodiment.

While the drape 10 described hereinabove has been shown as having a generally rectangular shape, it should be recognized that the drape may be provided with substantially any peripheral shape and size without departing from the scope of the present invention. For example, referring now to FIG. 5, in an alternate embodiment, a drape 10' is provided with a lateral offset to substantially form a T-shape. The lateral offset is typically located within about the middle third of the longitudinal dimension $L_D$, or more particularly, at approximately the midpoint of $L_D$, as shown, to provide a drape "bottom" half which is narrower than the "top" half. This substantial T-shape may provide added convenience to the user. For example, a relatively wide top half may facilitate mounting the drape on pole 21 of FIG. 2, while also providing a wide barrier, while the relatively narrow "bottom" half reduces the amount of drape material hanging over the edge of the patient's bed. Drape 10' may be provided with a longitudinal dimension $L_D$ of about 110 inches (279 cm) to about 130 inches (330 cm), a first "top" transverse dimension $T_D1$ of about 90 inches (229 cm) to about 110 inches (279 cm), and a second "bottom" transverse dimension $T_D2$ of about 70 inches (178 cm) to about 90 inches (229 cm), with the lateral offset occurring within the middle third of the longitudinal dimension $L_D$. In a particular embodiment, $L_D$ is about 120 inches (305 cm), $T_D1$ is about 100 inches (254 cm), and $T_D2$ is about 80 inches (203 cm), with the lateral offset occurring at about the midpoint of $L_D$.

Drape 10' includes window 14 and cover 22, as discussed above with respect to FIGS. 1-4. As also shown, drape 10' may optionally include any number of additional features commonly found on many conventional surgical drapes, such as, for example, an absorbent reinforcement 54, with incise area demarcation 52 and/or incise area fenestration 50, a fluid control pouch 56, line holders (e.g., hook and loop fastener style) 58, and contoured armboard covers 60, etc.

Figure 6:
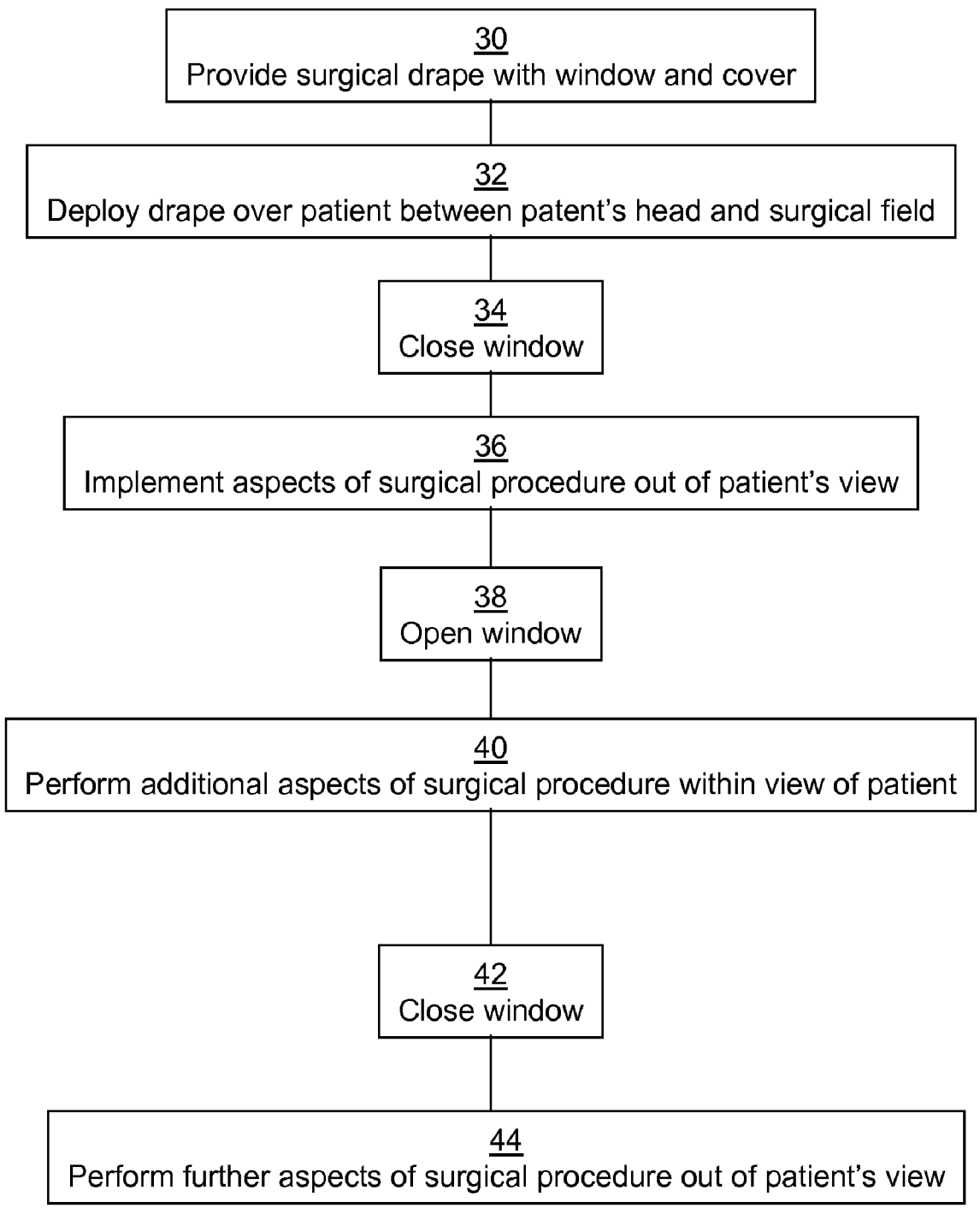
FIG. 6 is a flow chart of a method associated with the embodiment of FIGS. 1-5.

Turning to FIG. 6, a method of using an embodiment of the invention is shown and described. At 30, a surgical drape 10 is provided with a flexible transparent window 14, a removable cover 22, and a plurality of releasable fasteners 24. At 32, the drape is deployed using one or more conventional drape supports 21 to hang the drape over a patient, forming a substantially vertical barrier between the patient's head and surgical field 19. The window is closed 34 by using fasteners 24 to secure cover 22 over window 14 (FIG. 3). Aspects (e.g., preliminary aspects) of a surgical procedure are then implemented 36 in the surgical field 19. At 38, the window is opened by releasing fasteners 24 to allow the patient to view the surgical field 19. At 40, additional aspects of the surgical procedure are performed in view of the patient. The window 14 is then closed 42, and further (e.g., final) aspects of the surgical procedure are performed 44.

Although embodiments of the claimed invention are particularly suitable for Caesarian section procedures, they are not so limited. Rather, embodiments of the invention may be used with substantially any surgical procedure in which a patient is conscious and may wish to view some aspects of the surgery, and/or may be expected to answer questions during the surgery. Examples of such other surgical procedures may include hernia repairs, appendectomies, and/or orthopedic procedures.

It should be understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. A surgical drape for use in a surgical procedure on a patient, comprising:
   a flexible opaque sheet configured to satisfy barrier performance requirements of AAMI PB70:2003;
   said opaque sheet being configured for gas sterilization;
   a flexible transparent sheet disposed within said opaque sheet to form a window sized and shaped to permit the patient to view the surgical procedure therethrough;
   said window configured to satisfy barrier performance requirements of AAMI PB70:2003;
   said window being unopenably sealed along substantially its entire periphery to said opaque sheet in a manner configured to satisfy the barrier performance requirements of AAMI PB70:2003;
   said window being configured for gas sterilization;
   an opaque cover sized and shaped to substantially match that of said window;
   one or more releasable fasteners configured to releasably dispose said cover in superposed relation with said window, wherein said cover is configured to selectively cover and uncover said window;
   at least a portion of said cover being non-removably fastened to at least one of said opaque sheet and said window;
   a support engagement disposed along a margin of the drape; and
   a drape support disposed in operative engagement with said support engagement on opposite sides of said window, wherein said window is supported independently of the patient to form a substantially vertical barrier configured for being placed between the patient's head and a surgical field during the surgical procedure;
   said window configured for being selectively covered and uncovered during the surgical procedure to respectively prevent and permit the patient to view progress of the surgical procedure without affecting surgical access to the surgical field.

2. A surgical drape for use in a surgical procedure on a patient, comprising:
   a flexible opaque sheet configured to satisfy barrier performance requirements of AAMI PB70:2003;
   a flexible transparent sheet disposed within said opaque sheet to form a window sized and shaped to permit the patient to view the surgical procedure therethrough;
   said window configured to satisfy the barrier performance requirements of AAMI PB70:2003;
   a flexible, opaque cover sized and shaped to substantially match that of said window;
   one or more releasable fasteners configured to releasably dispose said cover in superposed relation with said window, to selectively cover and uncover said window;
   a support engagement disposed along a margin of the drape; and
   a drape support disposed in operative engagement with said support engagement on opposite sides of said window, wherein said window is supported independently of the patient to form a substantially vertical barrier configured for being placed between the patient's head and a surgical field during the surgical procedure;
   said window configured for being selectively covered and uncovered during the surgical procedure to respectively prevent and permit the patient to view progress of the surgical procedure without affecting surgical access to the surgical field.

3. The surgical drape of claim 2, wherein said window is sealed along its periphery to said opaque sheet in a manner configured to satisfy the barrier performance requirements of AAMI PB70:2003.

4. The surgical drape of claim 3, wherein said window is sealed along substantially its entire periphery to said opaque sheet in a manner configured to satisfy the barrier performance requirements of AAMI PB70:2003.

5. The surgical drape of claim 3, wherein at least a portion of said cover is non-removably fastened to at least one of said opaque sheet and said window.

6. The surgical drape of claim 2, wherein said window is sized and shaped to have:
   a longitudinal dimension within a range of about 10 to 20 inches (about 25 to 51 cm); and
   a transverse dimension within a range of about 20 to 30 inches (about 51 to 76 cm).

7. The surgical drape of claim 2, wherein said window is sized and shaped to have a viewing area within a range of about 200 to 600 square inches (about 1250 to 3900 square cm).

8. The surgical drape of claim 6, wherein said window has:
   a longitudinal dimension of about 15 inches (about 38 cm); and
   a transverse dimension of about 24 inches (about 61 cm).

9. The surgical drape of claim 7, wherein said window has a viewing area of about 360 square inches (about 2300 square cm).

10. The surgical drape of claim 7, where said drape has a longitudinal dimension within a range of at least about 110 inches (279 cm) to about 130 inches (330 cm), and a transverse dimension of at least about 90 inches (229 cm) to about 110 inches (279cm).

11. The surgical drape of claim 10, having a substantially rectangular periphery.

12. The surgical drape of claim 11, having a substantially T-shaped periphery.

13. The surgical drape of claim 2, wherein said window is disposed on the drape along a patient viewing axis.

14. The surgical drape of claim 2, wherein said support engagement comprises a hem disposed along an upper margin of the drape.

15. The surgical drape of claim 2, wherein said opaque sheet is configured for gas sterilization.

16. The surgical drape of claim 15, wherein said window is configured for gas sterilization.

17. The surgical drape of claim 16, wherein said cover is configured for gas sterilization.

18. The surgical drape of claim 2, comprising at least three releasable fasteners disposed in spaced relation along the periphery of said cover.

19. The surgical drape of claim 18, wherein said releasable fasteners are selected from the group consisting of snaps, ties, adhesives, hook and loop fasteners, and combinations thereof.

20. The surgical drape of claim 18, wherein said releasable fasteners comprise hook and loop fasteners.

21. The surgical drape of claim 2, wherein said opaque sheet has a patient side and a surgical side, and said cover is disposed on said surgical side.

22. The surgical drape of claim 2, wherein said opaque sheet has a patient side and a surgical side, and said cover is disposed on said patient side.

23. The surgical drape of claim 2, wherein the window is fabricated from a gas sterilizable polymeric material.

24. The surgical drape of claim 23, wherein the window is fabricated from a material selected from the group consisting of polyethylene (PE), polyvinylchloride (PVC), polypropylene (PP), and combinations or mixtures thereof.

25. The surgical drape of claim 2, comprising one or more features selected from the group consisting of an absorbent reinforcement, incise area demarcation, incise area fenestration, fluid control pouch, line holder, contoured armboard cover, and combinations thereof.

26. A surgical method comprising:
(a) providing a surgical drape having a flexible transparent window, a flexible cover sized and shaped to match the window, and a plurality of releasable fasteners configured to releasably secure the cover in superposed relation with the window, the drape meeting the barrier performance requirements of AAMI PB70:2003, and the drape including a support engagement disposed along a margin thereof;
(b) disposing a drape support in operative engagement with the support engagement on opposite sides of said window, to support the window independently of a patient to form a substantially vertical barrier;
(c) hanging the drape over the patient, forming a substantially vertical barrier between the patient's head and the patient's surgical field;
(d) closing the window using the releasable fasteners to secure the cover in superposed relation with the window;
(e) performing aspects of a surgical procedure in the surgical field, while the patient's view of the surgical field is blocked by the closed window;
(f) releasing the releasable fasteners to allow the patient to view the surgical field through the window;
(g) performing additional aspects of the surgical procedure in the surgical field, within view of the patient through the window;
(h) closing the window using the releasable fasteners to secure the cover in superposed relation with the window; and
(i) performing further aspects of the surgical procedure in the surgical field, while the patient's view of the surgical field is blocked by the closed window, wherein the window is selectively covered and uncovered during the surgical procedure to respectively prevent and permit the patient to view progress of the surgical procedure without affecting surgical access to the surgical field.

\* \* \* \* \*